United States Patent [19]

Carganico et al.

[11] Patent Number: 5,554,789

[45] Date of Patent: Sep. 10, 1996

[54] ARYLPROPIONIC DERIVATIVE, A PROCESS FOR THE PREPARATION AND THE USE THEREOF AS AN ANALGESIC AGENT

[75] Inventors: Germano Carganico, El Masnou; David Mauleon Casellas, Rubi; M. Luisa Garcia Perez, El Masnou, all of Spain

[73] Assignee: Laboratorios Menarini S.A., Barcelona, Spain

[21] Appl. No.: 428,231

[22] PCT Filed: Nov. 9, 1993

[86] PCT No.: PCT/EP93/03127

§ 371 Date: May 23, 1995

§ 102(e) Date: May 23, 1995

[87] PCT Pub. No.: WO94/11332

PCT Pub. Date: May 26, 1994

[30] Foreign Application Priority Data

Nov. 10, 1992 [ES] Spain ..................... 9202260

[51] Int. Cl.$^6$ ..................... C07C 59/76
[52] U.S. Cl. ..................... 562/460
[58] Field of Search ..................... 562/460; 514/570

[56] References Cited

FOREIGN PATENT DOCUMENTS

| 296 | 2/1970 | France . |
| 2580641 | 10/1986 | France . |

Primary Examiner—Paul J. Killos
Attorney, Agent, or Firm—Griffin, Butler, Whisenhunt & Kurtossy

[57] ABSTRACT

A novel arylpropionic derivative, i.e. the (+)-(S)-2-(3-Benzoylphenyl)propionic acid tromethamine salt, the process for the preparation thereof and the use thereof as an analgesic and antiinflammatory agent.

7 Claims, No Drawings

ARYLPROPIONIC DERIVATIVE, A PROCESS FOR THE PREPARATION AND THE USE THEREOF AS AN ANALGESIC AGENT

TECHNICAL FIELD

This invention relates to a novel arylpropionic acid salt, specifically the (+)-(S)-2-(3-benzoylphenyl)propionic acid tromethamine salt, of formula (I).

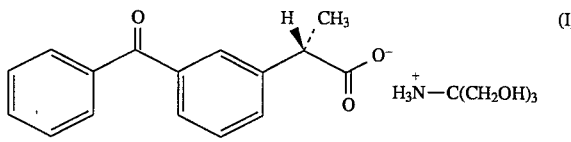

This invention also relates to the therapeutical use of this novel compound.

TECHNOLOGICAL BACKGROUND 2-(3-Benzoylphenyl)propionic acid, also known as ketoprofen (II), is a known nonsteroidal antiinflammatory drug having a potent analgesic and antipyretic action.

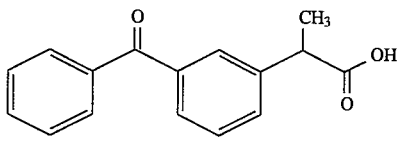

While ketoprofen has been marketed as a racemic mixture of its (+)-(S) and (−)-(R) enantiomers, it has been observed that its therapeutic action lies principally in the S enantiomer [Yamaguchi T. et al., Folia Pharmacol. Japon. 90, 295 (1987)]. Moreover, the (+)-(S) enantiomer of the ketoprofen has been claimed to be a faster acting and more potent analgesic than the racemic, administered doses being equal [Sunshine A. et al., WO 89/04658].

Structurally ketoprofen, similarly to other arylpropionic acids, has a lipophilic aromatic moiety which is responsible for its poor solubility in water and a free carboxylic group which has been said to relate to its ulcerogenic toxicity. These disadvantages can restrict its use, the poor solubility making its administration difficult either orally or by other means.

It has been reported that the disadvantages of the arylpropionic acids may substantially be overcome by means of salification with basic amino acids, such as the lysine salt with for ibuprofen [Kwan K. Ch. EP 424028] and ketoprofen [Metz G. EP 136470, BE 882889]; or metal salts, as it is the case of ketoprofen sodium or zinc salts [Fujimura H. et al., Oyo Yakuri, 13, 709 (1977) and Buxadé A. ES 2016503, respectively].

The therapeutic use of metal salts, such as the sodium salt, may be restricted as an excessive retention of said metal in the organism may be harmful, especially when the drug is administered frequently. In the case of the sodium salt, its high hygroscopicity can restrict the oral administration in form of tablets or other solid forms which are stable with time.

The compound of the present invention is a novel salt of the (+)-(S) enantiomer of ketoprofen for which there is no reference in literature. This salt was selected among a series of water soluble (+)-(S)-ketoprofen salts, such as the sodium salt, the aluminium salt, the L-lysine salt and the like. Surprisingly, compound (I) has a higher and faster solubility in water (>100% w/v) than any other (+)-(S)-ketoprofen salt. The combination of said two characteristics make this salt more advantageous than any other salt, for example the L-lysine salt is also highly soluble in water, however the dissolution rate thereof is significantly lower. Said characteristics allow the compound to be administered intramuscularly or intravenously, or as highly soluble tablets having a very fast dissolution rate. In addition to the ease of administration, the compound exhibits a faster onset of analgesic action, an enhanced analgesic response and a longer duration than racemic ketoprofen.

The novel derivative shows a fast and complete absorption in both animals and humans. The (+)-(S)-ketoprofen tromethamine salt also has a faster action and enhanced analgesic response than the racemic ketoprofen tromethamine salt.

For example, in a conventional analgesia animal model, the phenylbenzoquinone writhing test, compound (I) was evidenced to have the same analgesic effectiveness as a racemic ketoprofen double dose (Table I and II), the latter being administered intravenously as the salt and orally as the free acid.

The purification of arylpropionic acid salts with amine acid, particularly natural amine acids (L forms), by means of crystallization is known to be difficult [Bruzzese T. et al. U.S. Pat. No. 427,996]. In the case of the (S)-ketoprofen tromethamine salt, its higher solubility in ethanol (10% w/v) compared with e.g. the L-lysine salt (0.3% w/v), allows an easy crystallization from mixture of ethanol and an organic solvent such as ethyl acetate, to obtain the pure salt, completely free from the acid or tromethamine.

Thanks to what stated above, the (S)-ketoprofen tromethamine salt surprisingly overcomes the drawbacks of ketoprofen, both as the free acid and in the up to now known salified forms, as well as of (+)-(S)-ketoprofen, as the free acid as well as the salified forms. In fact, the compounds of the present invention has advantageous physico-chemical characteristics, such as: a very high and extremely fast water solubility at room temperature, an easy preparation and purification, a very low hygroscopicity, a physiologically compatible pH in aqueous solution, a high stability both in aqueous solution and in the solid state, no thermal (between 15° and 75° C.) or light degradations during a long time. Further advantages of the compound of the invention, compared with the other derivatives, are pharmacological properties such as: lower gastrolesive effects, lower toxicity and higher bioavailability, due to the high, fast absorption. Surprisingly, it has been observed that (+)-(S)-ketoprofen tromethamine salt is much less gastrolesive in animals than (+)-(S)-ketoprofen, (−)-(R)-ketoprofen and racemic ketoprofen. On the other hand, the administration of the (+)-(S)-ketoprofen tromethamine salt of the invention to humans gives raise to higher plasmatic levels of the active (+)-(S) enantiomer in a far shorter time than those obtained either by the administration of (+)-(S)-ketoprofen in form of the free acid or by administration of a double dose of racemic ketoprofen in form of the free acid. Moreover, said favourable characteristics give the compound of the invention a higher and faster analgesic action and allow its use in patients having gastro-intestinal, hypertension or cardiac problems, who cannot tolerate sodium administration.

All the characteristic properties of the compound (I) result in the same therapeutic efficacy as an analgesic while allowing lower doses than those required for either free or salified racemic ketoprofen and being markedly less gastrolesive than the corresponding free acid or the racemic ketoprofen.

Likewise said physico-chemical and pharmacokinetic properties result in compound (I) having a clear therapeutic advantage compared with the use of (+)-(S) enantiomer of ketoprofen in free acid form, claimed in the above mentioned patent [Sunshine A et al. WO 89/04658].

(+)-(S)-2-(3-Benzoylphenyl)propionic acid can be prepared according to the procedures described in current literature, either by enantio-selective synthesis [Fadel A., Synlett. 1, 48 (1992)] or by resolution of racemic ketoprofen by means of crystallization with chiral amines or by enzymatic methods [Nohira H. et al. EP 423467, Sih C. L. et al., EP 227078 and Carganico G. et al. Spanish Patent Nos. 9201189, 9201190 and 9201191].

The process for the preparation compound (I) is characterized by reacting (+)-(S)-2-(3-benzoylphenyl)propionic acid (III)

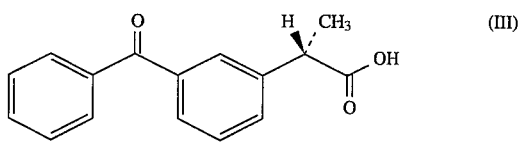

with tromethamine, $H_2NC(CH_2OH)_3$, in equimolar amounts. The reaction can be carried out in a solvent or in a mixture of polar solvents such as water, methanol, ethanol, acetonitrile, tetrahydrofuran or acetone. Preferably a mixture of water-methanol or ethanol is used. The reaction temperature may vary between 0° C. and the solvent reflux temperature, preferably between 15° and 40° C. for a time between 1 and 24 hours. The purification of the compound is carried out by means of crystallization in mixtures of organic solvents, such as ethanol-ethyl acetate, or ethanol-ethyl ether.

For therapeutic applications the compound is formulated in suitable pharmacoutical forms, using the conventional technology and excipients as described in Remington's Pharmaceutical Science Handbook, Mack Publishing Co. New York U.S.A. Examples of such forms include tablets, granules, solutions, syrups, injections and the like containing 1 to 1000 mg. per unit dose. The following examples show the preparation and the results of the tests for pharmacological activity of the compound of the present invention.

EXAMPLE 1

Preparation of the (+)-(S)-2-(3-benzoylohenyl)propionic acid tromethamine salt.

A solution of (+)-(S)-2-(3-benzoylphenyl)propionic acid (5.0 g, 19.7 mmol) in ethanol (15 ml) is added with a solution of tromethamine (2.4 g, 19.7 mmol) in water (8 ml). The mixture is stirred at room temperature for ½ hour, then evaporated to dryness, to give a semi-solid residue, which is redissolved in ethanol and then evaporated to dryness, to obtain a loose solid which is crystallized from ethanol-ethyl acetate, affording 6.8 g (92%) of the title compound as a white crystalline solid, with melting point 104.8°–105.1° C.

$[\alpha]_D^{20}$=–5.2° (c=1.47, methanol). IR (KBr): 3060, 1650, 1570, 1400, 1360, 1290, 1020, 720, 650 cm$^{-1}$.

N.M.R. $^1$H (300 MHz, CD$_3$OD) δ ppm: 1.45 (d, 3H); 3.64 (s, 6H); 3.66 (q, 1H); 7.41–7.80 (m, 9H).

Elemental analysis for $C_{20}H_{25}NO_6$: Calculated: C, 63.99%; H, 6.71%; N, 3.73%. Found: C, 63.60%; H, 6.40%; N, 3.73%.

EXAMPLE 2

Analgesic activity. Phenylbenzoquinone writhing test

This standard test, based on the procedure by Siegmund et al. [Proc. Soc. Exp. Biol. and Med., 95, 729 (1957)] allows to evaluate the analgesic effect of compound (I). In this test, Swiss male mice of 20 to 25 g are used, taken in random groups of 6 each. The product under examination is injected intravenously in the tail side vein. The product is administered dissolved in a physiological serum at a concentration suited to the dose to be administered, the volume thereof being 10 ml/kg. Immediately after the injection, a 1.03 mM phenylbenzoquinone solution in 1:20 ethanol:water is administered intraperitoneally, the volume being 10 ml/kg. Against each series of tests, a control group is administered systematically with the vehicle serum only. After an 5 min. interval from the introduction of the stated agent the writhings in the animal are counted over a 5 minute period. Lack of writhings indicates a successful outcome. The extent of analgesic protection can be measured in terms of the number of writhings compared with the control group. Table 1 below shows the analgesic effect as observed for compound (I) as well as the analgesic effect of the racemic ketoprofen tromethamine salt and of the (–)-(R) enantiomer by way of comparison. Table 2 shows the results obtained with compound (I) solubilized in physiological serum as compared to ketoprofen in homogeneous suspension (as a carboxymethylcellulose:tween mixture in a physiological serum) both being administered orally by esophageal catheter 30 minutes prior to the phenylbenzoquinone injection.

TABLE 1

| Analgesic effect. Phenylbenzoquinone test (intravenously) | | |
|---|---|---|
| Compound | Dose (mg/kg)$^a$ | % Inhibition |
| I | 0.15 | 71.0 ± 6.6 |
| (R,S)-ketoprofen tromethamine salt | 0.30 | 62.9 ± 11.7 |
| (–)-(R)-ketoprofen tromethamine salt | 0.15 | 23.7 ± 9.4 |

$^{a)}$Amount of ketoprofen injected in each administration of the salt.

TABLE 2

| Analgesic effect. Phenylbenzoguinone test (orally) | | |
|---|---|---|
| Compound | Dose (mg/kg)$^a$ | % Inhibition |
| I | 0.15 | 53.0 ± 12.7 |
| (R,S)-ketoprofen | 0.30 | 50.0 ± 7.8 |

$^{a)}$Amount of ketoprofen administered in each administration of the salt.

We claim:

1. (+)-(S)-2-(3-Benzoylphenyl)propionic acid tromethamine salt substantially free from the (–)-(R) enantiomers of the 2-(3-benzoylphenyl)propionic acid tromethamine salts, of formula (I)

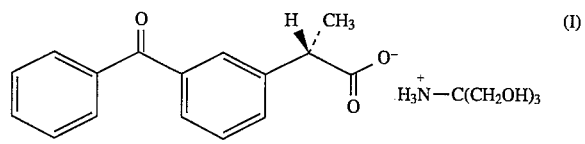

2. A process for the preparation of compound (I), claim 1 which process comprises reacting (+)-(S)-2-(3-benzoylphenyl)propionic acid (III)

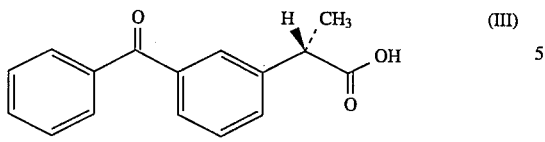

with tromethamine, $H_2NC(CH_2OH)_3$, in equimolar amount.

3. A process as claimed in claim 2, in which the reaction is carried out in a polar solvent or in a mixture of polar solvents.

4. A process as claimed in claim 3, in which the reaction is carried out in a mixture of water and methanol or ethanol.

5. A process as claimed in claim 2, characterized in that the reaction is carried out at a temperature between 0° C. and the solvent's reflux temperature, over a period between 1 and 24 hours.

6. A process as claimed in claim 5, in which the reaction temperature is between 15° and 40° C.

7. A pharmaceutical composition for producing a rapid and high analgesic response in humans, containing a therapeutically effective amount of the (+)(S)-2-(3 -benzoylphenyl)propionic acid tromethamine salt, substantially free from R enantiomer, and a non-toxic pharmaceutically acceptable carrier.

* * * * *